(12) United States Patent
Hwang et al.

(10) Patent No.: US 12,396,940 B2
(45) Date of Patent: Aug. 26, 2025

(54) ADDITIVE COMPOSITION FOR PREVENTING VITAMIN C PRECIPITATION

(71) Applicant: AMOREPACIFIC CORPORATION, Seoul (KR)

(72) Inventors: Yoonkyun Hwang, Yongin-si (KR); Jihye An, Yongin-si (KR); Dajeong Lee, Yongin-si (KR); Youngsuk Cho, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 607 days.

(21) Appl. No.: 17/642,129

(22) PCT Filed: Aug. 24, 2020

(86) PCT No.: PCT/KR2020/011223
§ 371 (c)(1),
(2) Date: Mar. 10, 2022

(87) PCT Pub. No.: WO2021/049775
PCT Pub. Date: Mar. 18, 2021

(65) Prior Publication Data
US 2022/0313588 A1    Oct. 6, 2022

(30) Foreign Application Priority Data

Sep. 11, 2019   (KR) .................. 10-2019-0113173
Aug. 18, 2020   (KR) .................. 10-2020-0103079

(51) Int. Cl.
*A61K 8/67* (2006.01)
*A61K 8/49* (2006.01)
*A61Q 19/02* (2006.01)

(52) U.S. Cl.
CPC ............ *A61K 8/676* (2013.01); *A61K 8/4953* (2013.01); *A61Q 19/02* (2013.01)

(58) Field of Classification Search
CPC ....... A61K 8/676; A61K 8/4953; A61Q 19/02
See application file for complete search history.

(56) References Cited

U.S. PATENT DOCUMENTS

| | | |
|---|---|---|
| 5,140,043 A | 8/1992 | Darr et al. |
| 2009/0292015 A1 | 11/2009 | Zhang et al. |

(Continued)

FOREIGN PATENT DOCUMENTS

| | | |
|---|---|---|
| EP | 0915695 B1 | 1/2003 |
| EP | 3677243 A1 | 7/2020 |

(Continued)

OTHER PUBLICATIONS

International Search Report for PCT/KR2020/011223 (Nov. 26, 2020).

(Continued)

*Primary Examiner* — Shirley V Gembeh
(74) *Attorney, Agent, or Firm* — Merchant & Gould P.C.

(57) ABSTRACT

The present specification describes an additive composition for preventing the precipitation of vitamin C in a cosmetic composition containing 15 wt % or more of vitamin C. The additive composition of the present invention comprises one or more of 3-O-ethyl ascorbic acid and caffeine as an active ingredient, and can thereby prevent precipitation of vitamin C even when a cosmetic composition is in cold storage. In addition, the additive composition according to the present invention can ameliorate the tingling irritation and stickiness that results from the inclusion of a high content of vitamin C.

13 Claims, 1 Drawing Sheet

(56) References Cited

U.S. PATENT DOCUMENTS

| | | | |
|---|---|---|---|
| 2015/0056255 A1* | 2/2015 | Ragot | A23F 5/36 8/405 |
| 2016/0015619 A1 | 1/2016 | Lee | |
| 2019/0151284 A1 | 5/2019 | Haga et al. | |
| 2021/0052481 A1 | 2/2021 | Kitaoka et al. | |

FOREIGN PATENT DOCUMENTS

| | | | |
|---|---|---|---|
| JP | 2010-163408 A | | 7/2010 |
| JP | WO2018/003850 A1 | | 7/2018 |
| KR | 10-2004-0085825 A | | 10/2004 |
| KR | 10-2007-0079166 A | | 8/2007 |
| KR | 10-2014-0101590 A | | 8/2014 |
| KR | 10-2015-0092102 A | | 8/2015 |
| KR | 20170138179 | * | 12/2017 |
| KR | 10-1833040 B1 | | 2/2018 |
| KR | 10-2018-0027444 A | | 3/2018 |
| KR | 10-1899927 B1 | | 9/2018 |
| KR | 10-2019-0013007 A | | 2/2019 |
| KR | 10-2019-0082242 A | | 7/2019 |
| WO | 2014/059228 A1 | | 4/2014 |
| WO | 2018/081790 A1 | | 5/2018 |
| WO | WO 2018/090149 | * | 5/2018 |
| WO | WO-2018090149 A1 * | 5/2018 | ........... A61K 31/132 |
| WO | WO 2019045413 | * | 3/2019 |
| WO | 2019/131892 A1 | | 7/2019 |

OTHER PUBLICATIONS

Monice M. Fiume et al., "Safety Assessment of Decyl Glucoside and Other Alkyl Glucosides as Used in Cosmetics", International Journal of Toxicology, 2013, vol. 32, pp. 22S-48S.

Monice M. Fiume et al., "Safety Assessment of Alkyl PEG/PPG Ethers as Used in Cosmetics", International Journal of Toxicology, 2016, vol. 35, pp. 60S-89S.

Office Action issued in the corresponding Korean Patent Application No. 10-2020-0103079, Apr. 3, 2024.

* cited by examiner

ADDITIVE COMPOSITION FOR PREVENTING VITAMIN C PRECIPITATION

The present application is a National Stage Application of PCT/KR2020/011223, filed Aug. 24, 2020, which claims the benefit of priority to Korean Patent Application No. 10-2019-0113173 filed on Sep. 11, 2019 and Korean Patent Application No. 10-2020-0103079 filed on Aug. 18, 2020 in the Republic of Korea, which applications are incorporated herein by reference. To the extent appropriate, a claim of priority is made to each of the above disclosed applications.

TECHNICAL FIELD

The present disclosure is directed to providing an additive composition for preventing precipitation of vitamin C in a cosmetic composition comprising a high content of vitamin C.

CROSS REFERENCE TO RELATED APPLICATIONS

The present application claims priority to Korean Patent Application No. 10-2019-0113173 filed on Sep. 11, 2019 and Korean Patent Application No. 10-2020-0103079 filed on Aug. 18, 2020 in the Republic of Korea, the disclosures of which are incorporated herein by reference.

BACKGROUND ART

Vitamin C, a typical ingredient for use in a cosmetic agent, is problematic in that it may be degenerated with ease by oxygen, heat, pH, or the like. Thus, vitamin C has been stored under the condition of refrigeration in order to prevent the above-mentioned problem. However, when a composition comprising a high content of vitamin C is refrigerated, vitamin C is precipitated due to low temperature, resulting in a problem of degradation of product quality. Therefore, a dissolution-improving agent, such as polyethylene glycol, has been used to overcome such a problem. However, the ingredients comprised in a conventionally used dissolution-improving agent have a disadvantage in that they may cause skin irritation. Under these circumstances, there is a need for developing a product causing no skin irritation and having an improved feeling of use, while preventing precipitation of vitamin C.

DISCLOSURE

Technical Problem

A technical problem to be solved by the present disclosure is to provide an additive composition for preventing precipitation of vitamin C in a cosmetic composition comprising a high content of pure vitamin C.

Another technical problem to be solved by the present disclosure is to provide an additive composition for imparting an improved feeling of use to a cosmetic composition comprising a high content of pure vitamin C.

Technical Solution

In one general aspect, there is provided an additive composition for preventing precipitation of vitamin C in a cosmetic composition comprising 15 wt % or more of vitamin C in order to solve the above-mentioned technical problem, the additive composition comprising at least one of 3-O-ethyl ascorbic acid and caffeine as an active ingredient.

Advantageous Effects

When the additive composition according to an embodiment of the present disclosure is added to a cosmetic composition comprising a high content of vitamin C, it is possible to prevent precipitation of vitamin C, even when the cosmetic composition is refrigerated for a long time, and thus it is possible to maintain high product quality. Particularly, according to the present disclosure, it is possible to prevent precipitation of vitamin C, even when a composition comprising a high content of vitamin C dissolved in 50 wt % or more of water is refrigerated. In addition, the additive composition according to the present disclosure alleviates a tingling sensation and stickiness of a composition comprising a high content of vitamin C, while providing the composition with increased stability.

BEST MODE

Exemplary embodiments now will be described more fully hereinafter with reference to the accompanying drawings. This disclosure may, however, be embodied in many different forms and should not be construed as limited to the exemplary embodiments set forth therein. However, the exemplary embodiments disclosed herein are provided so that the present disclosure may be thorough and complete and the technical gist of the present disclosure may be conveyed sufficiently to those skilled in the art. In addition, the present disclosure may be embodied in many different forms by those skilled in the art without departing from the scope of the present disclosure.

In one aspect, there is provided an additive composition for preventing precipitation of vitamin C in a cosmetic composition comprising 15 wt % or more of vitamin C.

As used herein, 'vitamin C (ascorbic acid)' comprises L-ascorbic acid as pure vitamin C. According to an embodiment, vitamin C has a molecular formula of 06H806 and is represented by the following Chemical Formula 1.

[Chemical Formula 1]

According to an embodiment, vitamin C not only provides an anti-oxidation effect but also protects the skin from UV irradiation, and inhibits activity of tyrosinase to prevent pigment deposition, thereby providing a skin whitening effect. In addition, vitamin C accelerates skin regeneration through the formation of collagen and improves skin wrinkles or elasticity.

According to an embodiment, the additive composition may comprise at least one of 3-O-ethyl ascorbic acid and caffeine as an active ingredient for preventing precipitation of vitamin C.

In another aspect, there is provided use of at least one of 3-O-ethyl ascorbic acid and caffeine for the preparation of an additive composition for preventing precipitation of vitamin C in a cosmetic composition comprising 15 wt % or more of vitamin C.

In still another aspect, there is provided a method for preventing precipitation of vitamin C, the method comprising adding an effective amount of at least one of 3-O-ethyl ascorbic acid and caffeine to a cosmetic composition comprising 15 wt % or more of vitamin C.

In still another aspect, there is provided at least one of 3-O-ethyl ascorbic acid and caffeine as an active ingredient for use in an additive composition for preventing precipitation of vitamin C in a cosmetic composition comprising 15 wt % or more of vitamin C.

According to an embodiment, 3-O-ethyl ascorbic acid may be added in an amount equal to or more than 0.0001 wt % and less than 30 wt %, based on the total weight of the cosmetic composition. For example, 3-O-ethyl ascorbic acid may be added in an amount of 0.0001 wt % or more, 0.001 wt % or more, 0.01 wt % or more, 0.1 wt % or more, 0.2 wt % or more, 0.3 wt % or more, 0.4 wt % or more, 0.5 wt % or more, 0.6 wt % or more, 0.7 wt % or more, 0.8 wt % or more, 0.9 wt % or more, 1 wt % or more, 2 wt % or more, 3 wt % or more, 4 wt % or more, 5 wt % or more, 6 wt % or more, 7 wt % or more, 8 wt % or more, 9 wt % or more, 10 wt % or more, 11 wt % or more, 12 wt % or more, 13 wt % or more, 14 wt % or more, 15 wt % or more, 16 wt % or more, 17 wt % or more, 18 wt % or more, 19 wt % or more, 20 wt % or more, 21 wt % or more, 22 wt % or more, 23 wt % or more, 24 wt % or more, 25 wt % or more, 26 wt % or more, 27 wt % or more, 28 wt % or more, or 29 wt % or more, based on the total weight of the cosmetic composition. In addition, 3-O-ethyl ascorbic acid may be added in an amount of less than 30 wt %, 29 wt % or less, 28 wt % or less, 27 wt % or less, 26 wt % or less, 25 wt % or less, 24 wt % or less, 23 wt % or less, 22 wt % or less, 21 wt % or less, 20 wt % or less, 19 wt % or less, 18 wt % or less, 17 wt % or less, 16 wt % or less, 15 wt % or less, 14 wt % or less, 13 wt % or less, 12 wt % or less, 11 wt % or less, 10 wt % or less, 9 wt % or less, 8 wt % or less, 7 wt % or less, 6 wt % or less, 5 wt % or less, 4 wt % or less, 3 wt % or less, 2 wt % or less, 1 wt % or less, 0.99 wt % or less, 0.9 wt % or less, 0.8 wt % or less, 0.7 wt % or less, 0.6 wt % or less, 0.5 wt % or less, 0.4 wt % or less, 0.3 wt % or less, 0.2 wt % or less, 0.15 wt % or less, 0.1 wt % or less, or 0.01 wt % or less, based on the total weight of the cosmetic composition. When 3-O-ethyl ascorbic acid is added in an amount of 30 wt % or more based on the total weight of the cosmetic composition, skin irritation may occur. When 3-O-ethyl ascorbic acid is added in an amount of less than 0.0001 wt %, it is not possible to obtain a sufficient effect of preventing precipitation of vitamin C.

According to an embodiment, caffeine may be added in an amount equal to or more than 0.0001 wt % and less than 3 wt %, based on the total weight of the cosmetic composition. For example, caffeine may be added in an amount of 0.0001 wt % or more, 0.001 wt % or more, 0.01 wt % or more, 0.1 wt % or more, 0.2 wt % or more, 0.3 wt % or more, 0.4 wt % or more, 0.5 wt % or more, 0.6 wt % or more, 0.7 wt % or more, 0.8 wt % or more, 0.9 wt % or more, 1.0 wt % or more, 1.1 wt % or more, 1.2 wt % or more, 1.3 wt % or more, 1.4 wt % or more, 1.5 wt % or more, 1.6 wt % or more, 1.7 wt % or more, 1.8 wt % or more, 1.9 wt % or more, 2.0 wt % or more, 2.1 wt % or more, 2.2 wt % or more, 2.3 wt % or more, 2.4 wt % or more, 2.5 wt % or more, 2.6 wt % or more, 2.7 wt % or more, 2.8 wt % or more, or 2.9 wt % or more, based on the total weight of the cosmetic composition. In addition, caffeine may be added in an amount of less than 3 wt %, 2.9 wt % or less, 2.8 wt % or less, 2.7 wt % or less, 2.6 wt % or less, 2.5 wt % or less, 2.4 wt % or less, 2.3 wt % or less, 2.2 wt % or less, 2.1 wt % or less, 2.0 wt % or less, 1.9 wt % or less, 1.8 wt % or less, 1.7 wt % or less, 1.6 wt % or less, 1.5 wt % or less, 1.4 wt % or less, 1.3 wt % or less, 1.2 wt % or less, 1.1 wt % or less, 1.0 wt % or less, 0.99 wt % or less, 0.9 wt % or less, 0.8 wt % or less, 0.7 wt % or less, 0.6 wt % or less, 0.5 wt % or less, 0.4 wt % or less, 0.3 wt % or less, 0.2 wt % or less, 0.15 wt % or less, 0.1 wt % or less, or 0.01 wt % or less, based on the total weight of the cosmetic composition. When caffeine is added in an amount of 3 wt % or more, caffeine may be precipitated at low temperature, and thus a separate system for preventing precipitation is required. When caffeine is added in an amount of less than 0.0001 wt %, it is not possible to obtain a sufficient effect of preventing precipitation of vitamin C.

According to an embodiment, the additive composition may comprise both 3-O-ethyl ascorbic acid and caffeine as active ingredients. In this case, the additive composition can effectively prevent precipitation of vitamin C, while it comprises 3-O-ethyl ascorbic acid and caffeine in a smaller amount as compared to a composition comprising either of ascorbic acid and caffeine. The total weight of 3-O-ethyl ascorbic acid and caffeine added to the cosmetic composition may be smaller than the weight of 3-O-ethyl ascorbic acid or caffeine of a composition comprising either of 3-O-ethyl ascorbic acid and caffeine. For example, the combined weight of 3-O-ethyl ascorbic acid and caffeine may be 0.9 times or less, 0.8 times or less, 0.7 times or less, 0.6 times or less, 0.5 times or less, 0.3 times or less, 0.2 times or less, 0.1 times or less, 0.05 times or less, 0.01 times or less, or 0.005 times or less of the weight of 3-O-ethyl ascorbic acid or caffeine of a composition comprising either of 3-O-ethyl ascorbic acid and caffeine. For example, the combined weight of 3-O-ethyl ascorbic acid and caffeine added to the cosmetic composition may be 0.00001-15 wt % based on the total weight of the cosmetic composition. Particularly, in an additive composition comprising both 3-O-ethyl ascorbic acid and caffeine as active ingredients, the combined weight of 3-O-ethyl ascorbic acid and caffeine added to the cosmetic composition may be 0.00001 wt % or more, 0.0001 wt % or more, 0.001 wt % or more, 0.01 wt % or more, 0.02 wt % or more, 0.03 wt % or more, 0.04 wt % or more, 0.05 wt % or more, 0.06 wt % or more, 0.07 wt % or more, 0.08 wt % or more, 0.09 wt % or more, 0.1 wt % or more, 0.2 wt % or more, 0.3 wt % or more, 0.4 wt % or more, 0.5 wt % or more, 0.6 wt % or more, 0.7 wt % or more, 0.8 wt % or more, 0.9 wt % or more, 1 wt % or more, 1.1 wt % or more, 1.2 wt % or more, 1.3 wt % or more, 1.4 wt % or more, 1.5 wt % or more, 2 wt % or more, 3 wt % or more, 4 wt % or more, 5 wt % or more, 6 wt % or more, 7 wt % or more, 8 wt % or more, 9 wt % or more, 10 wt % or more, 11 wt % or more, 12 wt % or more, 13 wt % or more, or 14 wt % or more, based on the total weight of the cosmetic composition. In addition, in an additive composition comprising both 3-O-ethyl ascorbic acid and caffeine as active ingredients, the combined weight of 3-O-ethyl ascorbic acid and caffeine added to the cosmetic composition may be 15 wt % or less, 14 wt % or less, 13 wt % or less, 12 wt % or less, 11 wt % or less, 10 wt % or less, 9 wt % or less, 8 wt % or less, 7 wt % or less, 6 wt % or less, 5 wt % or less, 4 wt % or less, 3 wt % or less, 2 wt % or less, 1.5 wt % or less, 1.4 wt % or less, 1.3 wt % or less, 1.2 wt % or less, 1.1 wt % or less, 1 wt % or less, 0.9 wt % or less, 0.8 wt % or less, 0.7 wt % or less, 0.6 wt % or less, 0.5 wt % or less, 0.4 wt % or less, 0.3 wt % or less, 0.2 wt % or less, 0.1 wt % or less, 0.09 wt % or less, 0.08 wt % or less, 0.07 wt % or less, 0.06 wt % or less, 0.05 wt % or less, 0.04 wt % or less, 0.03 wt % or less, 0.02 wt % or less, or 0.01 wt % or less, based on the total weight of the cosmetic composition.

According to an embodiment, the additive composition comprising both 3-O-ethyl ascorbic acid and caffeine as active ingredients may comprise 3-O-ethyl ascorbic acid and caffeine at a weight ratio of 1:0.01-1. Particularly, the additive composition may comprise 3-O-ethyl ascorbic acid and caffeine at a weight ratio of 1:0.1-0.7. More particularly, the additive composition may comprise 3-O-ethyl ascorbic acid and caffeine at a weight ratio of 1:0.001 or more, 1:0.01 or more, 1:0.05 or more, 1:0.1 or more, 1:0.2 or more, 1:0.3 or more, 1:0.4 or more, 1:0.5 or more, 1:0.6 or more, 1:0.7 or more, 1:0.8 or more, 1:0.9 or more, or 1:0.95 or more. In addition, the additive composition may comprise 3-O-ascrobic acid and caffeine at a weight ratio of 1:1 or less, 1: less than 1, 1:0.95 or less, 1:0.9 or less, 1:0.8 or less, 1:0.7 or less, 1:0.6 or less, 1:0.5 or less, 1:0.4 or less, 1:0.3 or less, 1:0.2 or less, 1:0.1 or less, or 1:0.01 or less.

The additive composition according to an embodiment of the present disclosure is added to a cosmetic composition comprising a high content of vitamin C, and prevents precipitation of vitamin C for a long time, when the cosmetic composition is refrigerated as well as is stored at room temperature. Thus, it is possible to retain the effect of vitamin C and to maintain product quality.

According to an embodiment, the additive composition may effectively alleviate stickiness or an irritative sensation of a cosmetic composition caused by incorporation of 15 wt % or more of vitamin C.

In still another aspect of the present disclosure, there is provided a cosmetic composition comprising the additive composition according to an embodiment of the present disclosure, and vitamin C, wherein vitamin C is comprised in an amount of 15 wt % or more based on the total weight of the cosmetic composition.

According to an embodiment, the cosmetic composition may comprise vitamin C in an amount of 15-33 wt % based on the total weight of the cosmetic composition. Particularly, the cosmetic composition may comprise vitamin C in an amount of 15 wt % or more, 16 wt % or more, 17 wt % or more, 18 wt % or more, 19 wt % or more, 20 wt % or more, 21 wt % or more, 22 wt % or more, 23 wt % or more, 24 wt % or more, 25 wt % or more, 26 wt % or more, 27 wt % or more, 28 wt % or more, 29 wt % or more, 30 wt % or more, 31 wt % or more, or 32 wt % or more, based on the total weight of the cosmetic composition. In addition, the cosmetic composition may comprise vitamin C in an amount of 33 wt % or less, 32 wt % or less, 31 wt % or less, 30 wt % or less, 29 wt % or less, 28 wt % or less, 27 wt % or less, 26 wt % or less, 25 wt % or less, 24 wt % or less, 23 wt % or less, 22 wt % or less, 21 wt % or less, 20 wt % or less, 19 wt % or less, 18 wt % or less, 17 wt % or less, or 16 wt % or less, based on the total weight of the cosmetic composition.

According to an embodiment, the additive composition may be used in an amount of 0.01-30 wt % based on the total weight of the cosmetic composition. Particularly, the additive composition may be used in an amount of 0.01 wt % or more, 0.1 wt % or more, 0.2 wt % or more, 0.3 wt % or more, 0.4 wt % or more, 0.5 wt % or more, 0.6 wt % or more, 0.7 wt % or more, 0.8 wt % or more, 0.9 wt % or more, 1 wt % or more, 2 wt % or more, 3 wt % or more, 4 wt % or more, 5 wt % or more, 6 wt % or more, 7 wt % or more, 8 wt % or more, 9 wt % or more, 10 wt % or more, 11 wt % or more, 12 wt % or more, 13 wt % or more, 14 wt % or more, 15 wt % or more, 16 wt % or more, 17 wt % or more, 18 wt % or more, 19 wt % or more, 20 wt % or more, 21 wt % or more, 22 wt % or more, 23 wt % or more, 24 wt % or more, 25 wt % or more, 26 wt % or more, 27 wt % or more, 28 wt % or more, or 29 wt % or more, based on the total weight of the cosmetic composition. In addition, the additive composition may be used in an amount of 30 wt % or less, 29 wt % or less, 28 wt % or less, 27 wt % or less, 26 wt % or less, 25 wt % or less, 24 wt % or less, 23 wt % or less, 22 wt % or less, 21 wt % or less, 20 wt % or less, 19 wt % or less, 18 wt % or less, 17 wt % or less, 16 wt % or less, 15 wt % or less, 14 wt % or less, 13 wt % or less, 12 wt % or less, 11 wt % or less, 10 wt % or less, 9 wt % or less, 8 wt % or less, 7 wt % or less, 6 wt % or less, 5 wt % or less, 4 wt % or less, 3 wt % or less, 2 wt % or less, 1 wt % or less, 0.9 wt % or less, 0.8 wt % or less, 0.7 wt % or less, 0.6 wt % or less, 0.5 wt % or less, 0.4 wt % or less, 0.3 wt % or less, 0.2 wt % or less, or 0.1 wt % or less, based on the total weight of the cosmetic composition. When the additive composition is used in an amount of less than 0.01 wt % based on 100 wt % of the cosmetic composition, it is not possible to obtain a sufficient effect of preventing precipitation of vitamin C. When the additive composition is used in an amount of larger than 30 wt %, it may cause degradation of a feeling of use.

According to an embodiment, the cosmetic composition may further comprise oil. According to an embodiment, the oil may be comprised in the form of an oil layer covering the surface of the cosmetic composition comprising vitamin C. Particularly, any oil may be used, as long as it can be used for a cosmetic composition. For example, the oil may be one satisfying the following Mathematical Formula 1.

$$N_o/(N_c+N_{si}) \leq 0.1 \qquad \text{[Mathematical Formula 1]}$$

wherein $N_o$ represents the number of oxygen atoms in the molecule, $N_c$ is the number of carbon atoms in the molecule, and $N_{si}$ represents the number of silicon atoms in the molecule.

According to an embodiment, the oil may comprise at least one selected from the group consisting of dimethicone, caprylic/capric triglyceride, methyl trimethicone, hydrogenated C6-14 olefin polymers, diphenylsiloxyphenyl trimethicone, C18-21 alkanes, phenyl trimethicone, cyclomethicone, cyclopentasiloxane, hydrogenated polyisobutene, 2-octyl dodecarol, dicaprylyl carbonate, triethylhexanoin, sucrose polycottonseedate and natural oil.

According to an embodiment, natural oil may be vegetable oil. More particularly, natural oil may be at least one selected from the group consisting of *Helianthus annuus* (sunflower) seed oil, *Camellia japonica* seed oil, olive oil, grapeseed oil, *Limnanthes alba* seed oil, *Borago officinalis* seed oil, squalane, jojoba oil, *Passiflora incarnata* seed oil, *Panax ginseng* seed oil and fermented *Camellia japonica* seed oil.

According to an embodiment, the cosmetic composition may comprise oil in an amount of 0-54 wt % based on the total weight of the cosmetic composition. Particularly, the content of oil may be 0 wt % or more, 0.01 wt % or more, 0.1 wt % or more, 1 wt % or more, 2 wt % or more, 3 wt % or more, 4 wt % or more, 5 wt % or more, 6 wt % or more, 7 wt % or more, 8 wt % or more, 9 wt % or more, 10 wt % or more, 11 wt % or more, 12 wt % or more, 13 wt % or more, 14 wt % or more, 15 wt % or more, 16 wt % or more, 17 wt % or more, 18 wt % or more, 19 wt % or more, 20 wt % or more, 21 wt % or more, 22 wt % or more, 23 wt % or more, 24 wt % or more, 25 wt % or more, 26 wt % or more, 27 wt % or more, 28 wt % or more, 29 wt % or more, 30 wt % or more, 31 wt % or more, 32 wt % or more, 33 wt % or more, 34 wt % or more, 35 wt % or more, 36 wt % or more, 37 wt % or more, 38 wt % or more, 39 wt % or more, 40 wt % or more, 41 wt % or more, 42 wt % or more, 43 wt % or more, 44 wt % or more, 45 wt % or more, 46 wt % or more, 47 wt % or more, 48 wt % or more, 49 wt % or more, 50 wt % or more, 51 wt % or more, 52 wt % or more, or 53 wt % or more, based on the total weight of the cosmetic composition. In addition, the content of oil may be 54 wt % or less, 53 wt % or less, 52 wt % or less, 51 wt % or less, 50 wt % or less, 49 wt % or less, 48 wt % or less, 47 wt % or less, 46 wt % or less, 45 wt % or less, 44 wt % or less, 43 wt % or less, 42 wt % or less, 41 wt % or less, 40 wt % or less, 39 wt % or less, 38 wt % or less, 37 wt % or less, 36 wt % or less, 35 wt % or less, 34 wt % or less, 33 wt % or less, 32 wt % or less, 31 wt % or less, 30 wt % or less, 29 wt % or less, 28 wt % or less, 27 wt % or less, 26 wt % or less, 25 wt % or less, 24 wt % or less, 23 wt % or less, 22 wt % or less, 21 wt % or less, 20 wt % or less, 19 wt % or less, 18 wt % or less, 17 wt % or less, 16 wt % or less, 15 wt % or less, 14 wt % or less, 13 wt % or less, 12 wt % or less, 11 wt % or less, 10 wt % or less, 9 wt % or less, 8 wt % or less, 7 wt % or less, 6 wt % or less, 5 wt % or less, 4 wt % or less, 3 wt % or less, 2 wt % or less, 1 wt % or less, or 0.1 wt % or less, based on the total weight of the cosmetic composition. When the cosmetic composition comprises oil in an amount of larger than 54 wt %, the content of vitamin C comprised in the cosmetic composition is reduced relatively. Thus, in this case, it is difficult to provide a cosmetic composition comprising a high content of vitamin C.

According to an embodiment, the cosmetic composition may comprise a surfactant. When the cosmetic composition comprises oil according to an embodiment, it may comprise a surfactant in an amount of less than 2 wt % based on the total weight of the cosmetic composition. More particularly, the cosmetic composition may comprise a surfactant in an amount of less than 2 wt %, 1.9 wt % or less, 1.8 wt % or less, 1.7 wt % or less, 1.6 wt % or less, 1.5 wt % or less, 1.4 wt % or less, 1.3 wt % or less, 1.2 wt % or less, 1.1 wt % or less, 1.0 wt % or less, 0.9 wt % or less, 0.8 wt % or less, 0.7 wt % or less, 0.6 wt % or less, 0.5 wt % or less, 0.4 wt % or less, 0.3 wt % or less, 0.2 wt % or less, 0.1 wt % or less, 0.05 wt % or less, or 0.01 wt % or less, based on the total weight of the cosmetic composition. In a variant, the cosmetic composition may comprise no surfactant. In addition, according to an embodiment, the surfactant for use in the cosmetic composition may be any surfactant with no particular limitation, as long as the surfactant does not inhibit the effect of preventing precipitation of vitamin C, when being added to the cosmetic composition comprising a high content of vitamin C. Particularly, the surfactant that may be used according to an embodiment of the present disclosure may have a turbidity of less than 850 NTU, when the turbidity is determined by introducing the composition to a 22 mL glass container, adding caprylic/capric triglyceride thereto in an amount of 10 wt % based on the total weight of the composition, shaking the resultant mixture 10 times, storing the resultant mixture at room temperature (21-23° C.) for 45 minutes, and measuring the turbidity by using Nephelometer (instrument: HI98703, Turbidity Portable Meter, available from HANNA). Meanwhile, the surfactant that may be used according to an embodiment of the present disclosure may have a turbidity of less than 20 NTU, when the turbidity is determined by introducing the composition to a 22 mL glass container, adding caprylic/capric triglyceride thereto in an amount of 10 wt % based on the total weight of the composition, shaking the resultant mixture 10 times, storing the resultant mixture at room temperature (21-23° C.) for 12 hours, and measuring the turbidity by using Nephelometer (instrument: HI98703, Turbidity Portable Meter, available from HANNA). More particularly, the surfactant may comprise at least one selected from the group consisting of Polysorbate 20, caprylyl/capryl glucoside-water and PPG-13-decyltetradeceth-24.

According to an embodiment, the cosmetic composition may further comprise a fat-soluble antioxidant material. The fat-soluble antioxidant material may comprise any fat-soluble antioxidant material used for a cosmetic composition. For example, the fat-soluble antioxidant material may comprise at least one selected from the group consisting of tocopherol, lycopene, beta-carotene and retinol.

When the cosmetic composition comprises oil according to an embodiment, it may further comprise a thickener. The thickener may be any thickener with no particular limitation, as long as it does not affect the interlayer separation between an aqueous phase and an oil phase, when oil is added to the cosmetic composition. For example, the thickener may comprise at least one selected from the group consisting of hyaluronate, xanthane gum, beta-glucan, sodium polyacrylate-hydrogenated polydecene-PPG-5-laureth-5, ammonium acryloyldimethyltaurate/VP copolymer, hydroxyethyl acrylate/sodium acryloyldimethyltaurate copolymer, butylene glycol-PEG-240/HDI copolymer bis-decyltetradeceth-20 ether-purified water-tocopherol-potassium laurate and Biosaccharide Gum-1.

According to an embodiment, the cosmetic composition may be for use in skin whitening.

The composition according to an embodiment of the present disclosure may be a composition for external use on skin comprising the active ingredients.

As used herein, the term 'skin' means a tissue covering the body surface of an animal and is used in its broadest concept comprising not only a tissue covering the body surface, such as face or body, but also scalp and hair.

According to an embodiment, the cosmetic composition according to the present disclosure may be formulated with a cosmetically or dermatologically acceptable medium or base. The formulation may comprise any formulation suitable for local application. For example, the composition may be provided in the form of a solution, gel, solid, anhydride paste, emulsion prepared by dispersing an oil phase in an aqueous phase, suspension, microemulsion, microcapsules, microgranules or ionic (liposome) and non-ionic sachet dispersant, or provided in the form of a cream, skin, lotion, powder, ointment, spray or conceal stick. In addition, the cosmetic composition may be used in the form of foam or an aerosol composition further comprising a compressed propellant. Such composition may be obtained by the methods generally known to those skilled in the art.

According to an embodiment, the cosmetic composition according to the present disclosure may comprise other ingredients that may not adversely affect the main effect of the present disclosure, preferably impart a synergic effect to the main effect, in combination with the active ingredients. Such ingredients other than the active ingredients may be selected and blended with ease by those skilled in the art depending on the particular formulation or purpose of use of the cosmetic composition. In addition, according to an embodiment, the cosmetic composition according to the present disclosure may further comprise other ingredients used conventionally for a cosmetic composition, if necessary, in combination with the above-mentioned ingredients. For example, such ingredients may comprise a moisturizing agent, emollient, organic and inorganic pigments, organic powder, UV-absorbing agent, preservative, sterilizing agent, antioxidant, plant extract, pH modifier, alcohol, colorant, fragrance, blood flow-stimulating agent, coolant, anti-perspirant, purified water, or the like. However, the ingredients that may be incorporated to the cosmetic composition according to the present disclosure are not limited to the above-listed ingredients. In addition, the ingredients may be used in a predetermined amount without detracting from the objects and effects of the present disclosure.

The composition according to an embodiment of the present disclosure may be a food composition comprising the active ingredients.

For example, the composition may be processed into functional food, such as fermented milk, cheese, yogurt, juice, probiotics or health-aid food, and may be used in the form of various food additives. According to an embodiment, the composition may be a health-aid food composition.

According to an embodiment, the health-aid food composition may be formulated into the form of pills, capsules, tablets, granules, caramels, drink, or the like. According to another embodiment, the composition may be processed into the form of a liquid, powder, granules, tablets, tea bags, or the like. The composition may be administrated through various methods, such as simple drinking, injection administration, spraying or squeezing. The composition may comprise other ingredients that may impart a synergic effect to the main effect without detracting from the main effect of the present disclosure. For example, the composition may further comprise additives, such as fragrance, pigment, sterilizing agent, antioxidant, preservative, moisturizing agent, thickener, inorganic salt, emulsifier and synthetic polymer materials in order to improve the physical properties. In addition, the composition may further comprise adjuvants, such as water-soluble vitamins, oil-soluble vitamins, polymer peptides, polysaccharides and seaweed extract. Such ingredients may be selected and blended with ease by those skilled in the art depending on the particular formulation or purpose of use of the composition. The amount of such ingredients may be selected without detracting from the objects and effects of the present disclosure. For example, the ingredients may be added in an amount of 0.0001-99.9 wt % based on the total weight of the composition.

The composition according to an embodiment of the present disclosure may be a pharmaceutical composition comprising the active ingredients. The pharmaceutical composition may further comprise pharmaceutical adjuvants, such as a preservative, stabilizer, hydrating agent or emulsification accelerator, salt for controlling osmotic pressure and/or a buffering agent, and other therapeutically useful substances.

According to an embodiment, the pharmaceutical composition may be formulated into a composition for oral administration, and particular examples thereof comprise tablets, pills, hard and soft capsules, liquid, suspension, emulsion, syrup, powder, micropowder, microparticles, granules, pellets, or the like. Such formulations may comprise a surfactant, diluent (e.g. lactose, dextrose, sucrose, mannitol, sorbitol, cellulose and glycine), a lubricant (e.g. silica, talc, stearic acid and magnesium or calcium salts thereof, and polyethylene glycol), or the like, in addition to the active ingredients. In addition, tablets may comprise a binding agent, such as magnesium aluminum silicate, starch paste, gelatin, tragacanth, methyl cellulose, sodium carboxymethyl cellulose or polyvinyl pyrrolidone. If necessary, tablets may comprise a pharmaceutical additive, comprising a disintegrating agent, such as starch, agar, alginic acid or sodium salt thereof, an absorbing agent, coloring agent, flavoring agent, sweetening agent, or the like. Such tablets may be prepared by conventional mixing, granulation or coating processes.

According to an embodiment, the pharmaceutical composition may be formulated into a composition for parenteral administration. The composition for parenteral administration may be provided as a formulation administered through a rectal, local, subcutaneous, transdermal route, or the like. For example, the formulation may be an injection formulation, drop, ointment, lotion, gel, cream, spray, suspension, emulsion, suppository, patch, or the like, but is not limited thereto.

According to an embodiment, the effective administration dose of the pharmaceutical composition may be varied with age, sex and body weight of a subject to be treated, particular disease or pathological condition to be treated, severity of a disease or pathological condition, administration route or judgement of a prescriber. Determination of a suitable dose may be made by those skilled in the art based on the above-mentioned factors. For example, the pharmaceutical composition may be administered in a daily dose of 1 mg/kg/day-10 g/kg/day, or 5 mg/kg/day-100 mg/kg/day, but the scope of the present disclosure is not limited thereto.

Modes for Invention

Hereinafter, the present disclosure will be explained in more detail with reference to examples. However, the following examples are for illustrative purposes only. In addition, it will be apparent to those skilled in the art that the scope of the present disclosure is not limited to the following examples.

Test Example 1

The cosmetic composition according to an embodiment of the present disclosure was prepared as follows. Then, it was determined whether an effect of preventing precipitation of vitamin C was realized or not by the addition of the additive composition according to an embodiment of the present disclosure.

First, the ingredients were mixed with water successively according to the composition as shown in the following Table 1 so that they might be dissolved completely. Next, each composition was introduced to a 20 mL vial, and then determined whether precipitation occurred or not, while being stored under refrigeration (5° C.) for 4 weeks. The trade name of vitamin C used for each composition is ascorbic acid ultrafine powder, that of 3-O-ethyl ascorbic acid is COS-VCE-K, and that of caffeine is NATURAL CAFFEINE ANHYDROUS FORM.

TABLE 1

| INCI | EX. 1 | Ex. 2 | Ex. 3 | Ex. 4 | Ex. 5 | Comp. Ex. 1 | Comp. Ex. 2 |
|---|---|---|---|---|---|---|---|
| PURIFIED WATER | To 100 | To 100 | To 100 | To 100 | To 100 | To 100 | To 100 |
| DISODIUM EDTA | 0.05 | 0.05 | 0.05 | 0.05 | 0.05 | 0.05 | 0.05 |
| BUTYLENE GLYCOL | 10 | 10 | 10 | 10 | 10 | 10 | 10 |
| VITAMIN C (ASCORBIC ACID) | 15 | 15 | 15 | 20 | 23 | 15 | 10 |
| 3-O-ETHYL ASCORBIC ACID | 0.2 | — | 0.1 | 0.2 | 0.2 | — | — |
| CAFFEINE | — | 0.2 | 0.1 | — | — | — | — |
| STABILITY (REFRIGERATION) | No precipitation | No precipitation | No precipitation | No precipitation | No precipitation | Precipitation | Precipitation |

(Unit: wt %)

Figure 1:
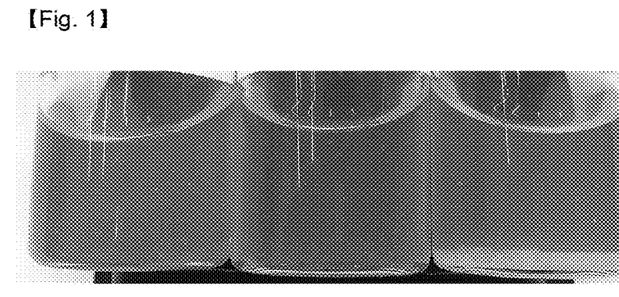
FIG. 1 illustrates whether precipitation of vitamin C occurs or not in Examples 1 and 2 according to the embodiments of the present disclosure and Comparative Example 1, sequentially as viewed from the left side, when they are refrigerated.
Figure 2:
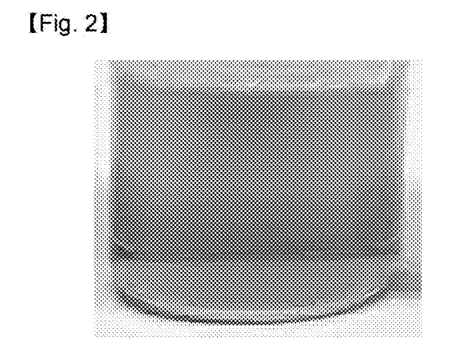
FIG. 2 illustrates whether precipitation of vitamin C occurs or not in Example 5 according to an embodiment of the present disclosure, when it is refrigerated.

As can be seen from Table 1, in the case of Comparative Example 1 comprising a high content (15 wt % or more) of pure vitamin C, precipitation of vitamin C occurs upon refrigeration. On the contrary, since at least one of 3-O-ethyl ascorbic acid and caffeine is added to each of Examples 1-5 according to an embodiment of the present disclosure, each composition causes no precipitation of vitamin C upon refrigeration, even though it comprises a high content (15 wt % or more) of pure vitamin C. FIG. 1 illustrates whether precipitation of vitamin C occurs or not in Examples 1 and 2 and Comparative Example 1, sequentially as viewed from the left side, and FIG. 2 illustrates the test result of Example 5.

The effect of preventing precipitation was determined by introducing each composition to a 20 mL vial and checking whether precipitation occurred or not by the naked eyes, while storing each composition under refrigeration (5° C.) for 4 weeks.

The effect of alleviating an irritative sensation was determined by allowing twenty females in their twenties or thirties to shake each of the compositions comprising vitamin C and an oil layer, to apply each composition onto the skin, and to evaluate whether they felt any irritative sensation or not.

TABLE 2

| INCI | Ex. 6 | Ex. 7 | Ex. 8 | Comp. Ex. 3 |
|---|---|---|---|---|
| PURIFIED WATER | To 100 | To 100 | To 100 | To 100 |
| DISODIUM EDTA | 0.05 | 0.05 | 0.05 | 0.05 |
| BUTYLENE GLYCOL | 10 | 10 | 10 | 10 |
| VITAMIN C (ASCORBIC ACID) | 15 | 15 | 15 | 15 |
| 3-O-ETHYL ASCORBIC ACID | 0.2 | — | 5 | — |
| CAFFEINE | — | 0.2 | — | — |
| DIMETHICONE | 4 | 4 | 4 | — |
| SQUALANE | 1 | 1 | 1 | — |
| ETHOXYDIGLYCOL | — | — | — | 5.2 |
| IRRITATIVE SENSATION | No | No | No | Strong |
| PRECIPITATION | No precipitation | No precipitation | No precipitation | No precipitation |
| RETENTION OF EFFECT | Retention | Retention | Retention | Reduced effect |

(Unit: wt %)

Test Example 2

The cosmetic composition according to an embodiment of the present disclosure was prepared as follows, and was determined in terms of an effect of preventing precipitation of vitamin C and an effect of alleviating an irritative sensation after adding the additive composition according to an embodiment of the present disclosure thereto.

First, the ingredients of aqueous part were mixed with water successively according to the composition as shown in the following Table 2 so that they might be dissolved completely, and then the oil part ingredient, dimethicone or squalene, was introduced thereto and mixed therewith.

As can be seen from Table 2, since 3-O-ethyl ascorbic acid or caffeine is added to each of Examples 6-8 according to the embodiments of the present disclosure, each composition causes no irritative sensation, even though it comprises a high content of vitamin C. In addition, no precipitation of vitamin C occurs even after storing each of Examples 6-8 for a long time, and each composition retains its effect. Therefore, it is possible to provide a high-content vitamin C composition having a low irritative sensation and a good feeling of use by using the additive composition according to an embodiment of the present disclosure. On the contrary, Comparative Example 3 comprising neither 3-O-ethyl ascorbic acid nor caffeine added thereto but comprising ethoxydiglycol to prevent precipitation causes no precipitation of vitamin C but shows a high irritative sensation. In addition, since each of Examples 6-8 has a layered structure in which oil is stacked on the top of the vitamin C composition, it prevents oxidation of vitamin C and retains the effect. When a high-content vitamin C cosmetic composition further comprises such an oil layer, it is possible to increase the service life of the cosmetic composition by virtue of an effect of preventing oxidation of vitamin C. On the contrary, Comparative Example 3 prevents precipitation but is susceptible to oxidation due to the lack of oil, and thus it causes significant degradation of its effect during long-term storage.

Test Example 3

The turbidity of a composition comprising a surfactant or not according to an embodiment of the present disclosure was determined by the following method.

Particularly, the ingredients of aqueous part were mixed with water successively according to the composition as shown in the following Table 3 and Table 4 so that they might be dissolved completely, and then the oil part ingredient, dimethicone or squalene, was introduced thereto and mixed therewith. The surfactant was introduced in the final stage of the preparation of aqueous part, but the order of introduction of a surfactant is not limited thereto, since it does not affect determination of turbidity.

Each of the compositions was introduced to a 22 mL glass container and caprylylic/capric triglyceride was added thereto in an amount of 10 wt % based on the total weight of the composition, the resultant mixture was shaken 10 times and stored at room temperature of 21-23° C. for 45 minutes, and then the turbidity of each composition was determined by using Nephelometer (instrument: HI98703, Turbidity Portable Meter, available from HANNA). In addition, each of the compositions was introduced to a 22 mL glass container and dimethicone or caprylylic/capric triglyceride was added thereto in an amount of 10 wt % based on the total weight of the composition, the resultant mixture was shaken 10 times and stored at room temperature of 21-23° C. for 12 hours, and then the turbidity of each composition was determined by using Nephelometer (instrument: HI98703, Turbidity Portable Meter, available from HANNA). The reason why the turbidity was determined after allowing each composition to stand for 45 minutes and 12 hours, separately, is that the time required for interlayer separation of each composition varies with the types of surfactant and oil.

TABLE 3

| INCI | Ex. 9 | Ex. 10 | Ex. 11 | Ex. 12 | Comp. Ex. 4 |
| --- | --- | --- | --- | --- | --- |
| PURIFIED WATER | To 100 | To 100 | To 100 | To 100 | To 100 |
| DISODIUM EDTA | 0.05 | 0.05 | 0.05 | 0.05 | 0.05 |
| BUTYLENE GLYCOL | 10 | 10 | 10 | 10 | 10 |
| VITAMIN C (ASCORBIC ACID) | 15 | 15 | 15 | 15 | 15 |
| 3-O-ETHYL ASCORBIC ACID | 0.2 | 0.2 | 0.2 | 0.2 | 0.2 |
| CAFFEINE | — | — | — | — | — |
| POLYSORBATE 20 | 0 | 0.2 | 0.5 | 2 | 3 |
| CAPRYLYL/CAPRYL GLUCOSIDE-WATER | — | — | — | — | — |
| PPG-13-DECYLTETRADECETH-24 | — | — | — | — | — |
| DIMETHICONE | 10 | 10 | 10 | 10 | 10 |
| CAPRYLIC/CAPRIC TRIGLYCERIDE | — | — | — | — | — |
| TURBIDITY AFTER 12 HOURS (NTU) | 2.43 | 2.63 | 3.08 | 3.24 | — |
| TURBIDITY AFTER 45 MINUTES (NTU) | 2.47 | 3.13 | 3.52 | 4.14 | Error generated |

(Unit: wt %)

TABLE 4

| INCI | Ex. 13 | Ex. 14 | Ex. 15 | Ex. 16 | Comp. Ex. 5 |
| --- | --- | --- | --- | --- | --- |
| PURIFIED WATER | To 100 | To 100 | To 100 | To 100 | To 100 |
| DISODIUM EDTA | 0.05 | 0.05 | 0.05 | 0.05 | 0.05 |
| BUTYLENE GLYCOL | 10 | 10 | 10 | 10 | 10 |
| VITAMIN C (ASCORBIC ACID) | 15 | 15 | 15 | 15 | 15 |
| 3-O-ETHYL ASCORBIC ACID | 0.2 | 0.2 | 0.2 | 0.2 | 0.2 |
| CAFFEINE | — | — | — | — | — |
| POLYSORBATE 20 | 0 | 0.2 | 0.5 | 2 | 3 |
| CAPRYLYL/CAPRYL GLUCOSIDE-WATER | — | — | — | — | — |
| PPG-13-DECYLTETRADECETH-24 | — | — | — | — | — |
| DIMETHICONE | — | — | — | — | — |
| CAPRYLIC/CAPRIC TRIGLYCERIDE | 10 | 10 | 10 | 10 | 10 |
| TURBIDITY AFTER 12 HOURS (NTU) | 2.97 | 5.2 | 10.5 | 10.7 | — |
| TURBIDITY AFTER 45 MINUTES (NTU) | 9.31 | 549 | 655 | 844 | Error generated |

(Unit: wt %)

TABLE 5

| INCI | Ex. 17 | Ex. 18 | Comp. Ex. 6 | Ex. 19 | Comp. Ex. 20 | Ex. 7 |
|---|---|---|---|---|---|---|
| PURIFIED WATER | To 100 | To 100 | To 100 | To 100 | To 100 | To 100 |
| DISODIUM EDTA | 0.05 | 0.05 | 0.05 | 0.05 | 0.05 | 0.05 |
| BUTYLENE GLYCOL | 10 | 10 | 10 | 10 | 10 | 10 |
| VITAMIN C (ASCORBIC ACID) | 15 | 15 | 15 | 15 | 15 | 15 |
| 3-O-ETHYL ASCORBIC ACID | — | — | — | — | — | — |
| CAFFEINE | 0.2 | 0.2 | 0.2 | 0.2 | 0.2 | 0.2 |
| POLYSORBATE 20 | — | — | — | — | — | — |
| CAPRYLYL/CAPRYL GLUCOSIDE-WATER | 0.2 | 2 | 3 | 0.2 | 2 | 3 |
| PPG-13-DECYLTETRADECETH-24 | — | — | — | — | — | — |
| DIMETHICONE | — | — | — | 10 | 10 | 10 |
| CAPRYLIC/CAPRIC TRIGLYCERIDE | 10 | 10 | 10 | — | — | — |
| TURBIDITY AFTER 12 HOURS (NTU) | 6.05 | 11.5 | — | 1.96 | 2.03 | — |
| TURBIDITY AFTER 45 MINUTES (NTU) | 127 | 511 | Error generated | — | — | Error generated |

(Unit: wt %)

TABLE 6

| INCI | Ex. 21 | Ex. 22 | Comp. Ex. 8 | Ex. 23 | Ex. 24 | Comp. Ex. 9 |
|---|---|---|---|---|---|---|
| PURIFIED WATER | To 100 | To 100 | To 100 | To 100 | To 100 | To 100 |
| DISODIUM EDTA | 0.05 | 0.05 | 0.05 | 0.05 | 0.05 | 0.05 |
| BUTYLENE GLYCOL | 10 | 10 | 10 | 10 | 10 | 10 |
| VITAMIN C (ASCORBIC ACID) | 15 | 15 | 15 | 15 | 15 | 15 |
| 3-O-ETHYL ASCORBIC ACID | — | — | — | — | — | — |
| CAFFEINE | 0.2 | 0.2 | 0.2 | 0.2 | 0.2 | 0.2 |
| POLYSORBATE 20 | — | — | — | — | — | — |
| CAPRYLYL/CAPRYL GLUCOSIDE-WATER | — | — | — | — | — | — |
| PPG-13-DECYLTETRADECETH-24 | 0.2 | 2 | 3 | 0.2 | 2 | 3 |
| DIMETHICONE | — | — | — | 10 | 10 | 10 |
| CAPRYLIC/CAPRIC TRIGLYCERIDE | 10 | 10 | 10 | — | — | — |
| TURBIDITY AFTER 12 HOURS (NTU) | 6.28 | 4.91 | — | 2.52 | 2.47 | — |
| TURBIDITY AFTER 45 MINUTES (NTU) | 312 | 640 | Error generated | — | — | Error generated |

(Unit: wt %)

As can be seen from the above results, each of the compositions comprising 2 wt % or less of a surfactant or comprising no surfactant according to an embodiment of the present disclosure shows a turbidity of less than 850 NTU after 45 minutes. In the case of a composition comprising 2 wt % or more of a surfactant, it shows a turbidity exceeding 850 NTU or causes an error due to a non-detectable range of turbidity. This suggests that it takes a long time to perform interlayer separation between an oil layer and an aqueous layer due to the surfactant and the effect of preventing oxidation of the vitamin C composition is not sufficient, and thus it is required that the service life of the composition is limited to several months or less.

Test Example 4

The cosmetic composition according to an embodiment of the present disclosure was prepared according to the composition as shown in the following Table 7 in the same manner as Test Example 1. Then, the cosmetic composition was determined in terms of an effect of preventing precipitation of vitamin C.

TABLE 7

| INCI | Ex. 25 | Ex. 26 |
|---|---|---|
| PURIFIED WATER | to 100 | to 100 |
| DISODIUM EDTA | 0.05 | 0.05 |
| BUTYLENE GLYCOL | — | — |
| VITAMIN C | 15 | 15 |
| 3-O-ETHYL ASCORBIC ACID | 0.05 | — |
| CAFFEINE | 0.05 | 0.2 |
| STABILITY (REFRIGERATION) | No precipitation | No precipitation |

(Unit: wt %)

As can be seen from the above results, Example 25 comprising both 3-O-ethyl ascorbic acid and caffeine shows an excellent effect of preventing precipitation of vitamin C, even though 3-O-ethyl ascorbic acid and caffeine are used in a smaller amount as compared to Example 26. In addition, it can be seen from the result of Example 26 that use of caffeine alone can prevent precipitation of vitamin C regardless of the presence of a polyol, such as butylene glycol.

The following embodiments are provided by the present disclosure.

According to the first embodiment, there is provided an additive composition for preventing precipitation of vitamin C in a cosmetic composition comprising 15 wt % or more of vitamin C, wherein the additive composition comprises at least one of 3-O-ethyl ascorbic acid and caffeine as an active ingredient.

According to the second embodiment, there is provided the additive composition as defined in the first embodiment, wherein 3-O-ethyl ascorbic acid is added in an amount equal to or more than 0.0001 wt % and less than 30 wt % based on the total weight of the cosmetic composition.

According to the third embodiment, there is provided the additive composition as defined in the first or the second embodiment, wherein caffeine is added in an amount of 0.0001-3 wt % based on the total weight of the cosmetic composition.

According to the fourth embodiment, there is provided the additive composition as defined in any one of the first to the third embodiments, wherein the additive composition comprises 3-O-ethyl ascorbic acid and caffeine as active ingredients, and the combined weight of 3-O-ethyl ascorbic acid and caffeine added to the cosmetic composition is 0.00001-15 wt % based on the total weight of the cosmetic composition.

According to the fifth embodiment, there is provided the additive composition as defined in any one of the first to the fourth embodiments, wherein the additive composition comprises 3-O-ethyl ascorbic acid and caffeine as active ingredients, and the weight ratio of 3-O-ethyl ascorbic acid to caffeine added to the cosmetic composition is 1:0.01-1.

According to the sixth embodiment, there is provided the additive composition as defined in any one of the first to the fifth embodiments, wherein the additive composition is added in an amount of 0.01-30 wt % based on 100 wt % of the cosmetic composition.

According to the seventh embodiment, there is provided the additive composition as defined in any one of the first to the sixth embodiments, which comprises use of the additive composition for alleviating stickiness of a cosmetic composition comprising 15 wt % or more of vitamin C.

According to the eighth embodiment, there is provided the additive composition as defined in any one of the first to the seventh embodiments, which comprises use of the additive composition for alleviating an irritative sensation of a cosmetic composition comprising 15 wt % or more of vitamin C.

According to the ninth embodiment, there is provided a cosmetic composition comprising the additive composition as defined in any one of the one to the eighth embodiments; and vitamin C, wherein vitamin C is comprised in an amount of 15 wt % or more based on the total weight of the cosmetic composition.

According to the tenth embodiment, there is provided the cosmetic composition as defined in the one to the ninth embodiments, which comprises vitamin C in an amount of 15-33 wt % based on the total weight of the cosmetic composition.

According to the eleventh embodiment, there is provided the cosmetic composition as defined in any one of the one to the tenth embodiments, which comprises the additive composition in an amount of 0.01-30 wt % based on the total weight of the cosmetic composition.

According to the twelfth embodiment, there is provided the cosmetic composition as defined in any one of the one to the eleventh embodiments, which further comprises oil.

According to the thirteenth embodiment, there is provided the cosmetic composition as defined in any one of the one to the twelfth embodiments, wherein the oil is comprised in the form of an oil layer covering the surface of the cosmetic composition comprising vitamin C.

According to the fourteenth embodiment, there is provided the cosmetic composition as defined in any one of the one to the thirteenth embodiments, wherein the oil satisfies the following Mathematical Formula 1:

$$N_o/(N_c+N_{si}) \leq 0.1 \qquad \text{[Mathematical Formula 1]}$$

wherein $N_o$ represents the number of oxygen atoms in the molecule, $N_c$ is the number of carbon atoms in the molecule, and $N_{si}$ represents the number of silicon atoms in the molecule.

According to the fifteenth embodiment, there is provided the cosmetic composition as defined in any one of the one to the fourteenth embodiments, wherein the oil comprises at least one selected from the group consisting of dimethicone, caprylic/capric triglyceride, methyl trimethicone, hydrogenated 06-14 olefin polymers, diphenylsiloxyphenyl trimethicone, C18-21 alkanes, phenyl trimethicone, cyclomethicone, cyclopentasiloxane, hydrogenated polyisobutene, 2-octyl dodecarol, dicaprylyl carbonate, triethylhexanoin, sucrose polycottonseedate and natural oil.

According to the sixteenth embodiment, there is provided the cosmetic composition as defined in any one of the one to the fifteenth embodiments, which comprises a surfactant in an amount of less than 2 wt % based on the total weight of the cosmetic composition.

According to the seventeenth embodiment, there is provided the cosmetic composition as defined in any one of the one to the sixteenth embodiments, wherein the surfactant comprises at least one selected from the group consisting of Polysorbate 20, caprylyl/capryl glucoside*water and PPG-13-decyltetradeceth-24.

According to the eighteenth embodiment, there is provided the cosmetic composition as defined in any one of the one to the seventeenth embodiments, which is for use in skin whitening.

It should be understood that the above-described embodiments are given by way of illustration only and the scope of the present disclosure is not limited to the above detailed description. In addition, various changes, modifications and substitutions within the scope of the present disclosure will become apparent to those skilled in the art.

The invention claimed is:

1. A method for preventing precipitation of vitamin C in a cosmetic composition comprising 15 wt % or more of vitamin C,
   wherein the method comprises adding an effective amount of 3-O-ethyl ascorbic acid and caffeine to the cosmetic composition,
   wherein the weight ratio of the 3-O-ethyl ascorbic acid to the caffeine added to the cosmetic composition is 1:0.01-1, and
   wherein the combined weight of the 3-O-ethyl ascorbic acid and the caffeine added to the cosmetic composition is 0.01-1 wt. % based on the total weight of the cosmetic composition.

2. The method according to claim 1, wherein the 3-O-ethyl ascorbic acid is added in an amount equal to or more than 0.001 wt % and less than 1.0 wt % based on the total weight of the cosmetic composition.

3. The method according to claim 1, wherein the caffeine is added in an amount equal to or more than 0.001 and less than 1.0 wt % based on the total weight of the cosmetic composition.

4. The method according to claim 1, wherein the 3-O-ethyl ascorbic acid and caffeine is added for alleviating stickiness of the cosmetic composition comprising 15 wt % or more of vitamin C.

5. The method according to claim 1, wherein the 3-O-ethyl ascorbic acid and caffeine is added for alleviating an irritative sensation of the cosmetic composition comprising 15 wt % or more of vitamin C.

6. The method according to claim 1, wherein the cosmetic composition comprises vitamin C in an amount of 15-33 wt % based on the total weight of the cosmetic composition.

7. The method according to claim 1, wherein the method further comprises adding an effective amount of oil to the cosmetic composition.

8. The method according to claim 7, wherein the oil is added in the form of an oil layer covering the surface of the cosmetic composition comprising vitamin C.

9. A method for preventing precipitation of vitamin C in a cosmetic composition comprising 15 wt % or more of vitamin C,
wherein the method comprises adding an effective amount of 3-O-ethyl ascorbic acid and caffeine to the cosmetic composition,
wherein the weight ratio of the 3-O-ethyl ascorbic acid to the caffeine added to the cosmetic composition is 1:0.01-1,
wherein the method comprises adding an effective amount of oil to the cosmetic composition, and
wherein the oil satisfies the following Mathematical Formula 1:

$$N_o/(N_c+N_{si}) \leq 0.1 \qquad \text{[Mathematical Formula 1]}$$

wherein $N_o$ represents the number of oxygen atoms in the molecule, $N_c$ is the number of carbon atoms in the molecule, and $N_{si}$ represents the number of silicon atoms in the molecule.

10. The method according to claim 7, wherein the oil comprises at least one selected from the group consisting of dimethicone, caprylic/capric triglyceride, methyl trimethicone, hydrogenated C6-14 olefin polymers, diphenylsiloxyphenyl trimethicone, C18-21 alkanes, phenyl trimethicone, cyclomethicone, cyclopentasiloxane, hydrogenated polyisobutene, 2-octyl dodecarol, dicaprylyl carbonate, triethylhexanoin, sucrose polycottonseedate and natural oil.

11. The method according to claim 1, wherein the cosmetic composition comprises a surfactant in an amount of less than 2 wt % based on the total weight of the cosmetic composition.

12. The method according to claim 11, wherein the surfactant comprises at least one selected from the group consisting of Polysorbate 20, caprylyl/capryl glucoside*water and PPG-13-decyltetradeceth-24.

13. The method according to claim 1, which is for skin whitening.

* * * * *